(12) United States Patent
Kim

(10) Patent No.: US 9,533,008 B2
(45) Date of Patent: Jan. 3, 2017

(54) DEVICE FOR GENERATING AND SUPPLYING GERMANIUM IONIC WATER

(71) Applicant: Dong Huen Kim, Sejong-si (KR)

(72) Inventor: Dong Huen Kim, Sejong-si (KR)

( * ) Notice: Subject to any disclaimer, the term of this patent is extended or adjusted under 35 U.S.C. 154(b) by 0 days.

(21) Appl. No.: 15/027,450

(22) PCT Filed: Sep. 26, 2014

(86) PCT No.: PCT/KR2014/009005
§ 371 (c)(1),
(2) Date: Apr. 6, 2016

(87) PCT Pub. No.: WO2015/056901
PCT Pub. Date: Apr. 23, 2015

(65) Prior Publication Data
US 2016/0243161 A1    Aug. 25, 2016

(30) Foreign Application Priority Data

Oct. 16, 2013 (KR) .................. 10-2013-0123029

(51) Int. Cl.
C02F 9/00      (2006.01)
A61K 33/24     (2006.01)
B01J 19/08     (2006.01)
C02F 1/32      (2006.01)
C02F 103/02    (2006.01)

(52) U.S. Cl.
CPC ............. *A61K 33/24* (2013.01); *B01J 19/088* (2013.01); *C02F 1/325* (2013.01); *B01J 2219/0805* (2013.01); *B01J 2219/089* (2013.01); *B01J 2219/0871* (2013.01); *C02F 2103/026* (2013.01); *C02F 2201/326* (2013.01); *C02F 2209/02* (2013.01); *C02F 2209/42* (2013.01)

(58) Field of Classification Search
CPC ............. C02F 2209/42; C02F 2103/026; C02F 2201/326; C02F 2209/02; C02F 1/32; B01J 2219/089; B01J 2219/0871; B01J 19/08
See application file for complete search history.

(56) References Cited

FOREIGN PATENT DOCUMENTS

| JP | 2007-105691 A | 4/2007 |
|---|---|---|
| KR | 10-1994-0010212 B1 | 10/1994 |
| KR | 10-2005-0100228 A | 10/2005 |
| KR | 10-0996277 B1 | 11/2010 |
| KR | 10-2012-0045950 A | 5/2012 |

OTHER PUBLICATIONS

CN 2201395 Y, Ionic water producer: Jun. 1995, China, Jinzhou Yan.*

* cited by examiner

*Primary Examiner* — Walter D Griffin
*Assistant Examiner* — Cameron Allen
(74) *Attorney, Agent, or Firm* — Rabin & Berdo, P.C.

(57) ABSTRACT

The present invention can supply a pulse to a pure germanium rod made of germanium so as to significantly increase concentration in a short period of time and shorten dissolving time, and relates to a device for generating and supplying germanium ionic water, which can promote the ionization of germanium.

3 Claims, 2 Drawing Sheets

DEVICE FOR GENERATING AND SUPPLYING GERMANIUM IONIC WATER

TECHNICAL FIELD

The present invention relates to a device for generating and supplying germanium ionic water, and more particularly, to a device for generating and supplying germanium ionic water that can generate and supply pure and stable germanium ionic water by using a semiconductor property of pure germanium (a high content of 99.999% or more) that is produced through a process of smelting germanium existing in ores of the natural system, can shorten solving time by supplying pulses to pure germanium rods of germanium and significantly improving the concentration of germanium in a short time so as to shorten solving time, and can quantitatively provide germanium at a stable concentration and a stable content because the ions of the germanium have sizes smaller than the sizes of organic germanium and ions melted in germanium mineral water and thermal water existing in the natural system and it ensures an excellent effect and a high content of germanium.

BACKGROUND ART

Many studies on the effects of germanium have been made in Japanese and numerous materials on germanium are present.

However, because germanium is extracted from organic materials to be supplied, it takes much time to extract germanium, and only several grams of germanium can be produced from several tons of organic material even when germanium is extracted from a large amount of organic materials, which increases the price of germanium and makes it difficult for people to purchase germanium.

Meanwhile, because even a small amount of germanium can provide various effects, Lourde spring of France shows many miraculous treatments even though it contains a very small amount of germanium.

Accordingly, because even a small amount of germanium extracted from organic materials is expensive, it is mixed with ferments or yeasts to be sold, and is coupled to ferments or yeasts to be absorbed in the human body.

However, the method of coupling germanium to the ferments or yeasts deteriorates absorption force as compared with ionized germanium ionic water.

Germanium may be extracted even from inorganic materials, and pure germanium may be extracted from germanium ores by heating the ores to the boiling point.

However, even in this case, germanium is coupled to ferments or yeasts to be taken, and powder germanium is supplied to a sauna bath to be effect to skin.

As a result, although germanium in the form of ions contained in mineral water and thermal water is safely taken, the prices of the mineral water and the thermal water are expensive so that ordinary persons cannot easily obtain them practically.

Therefore, a technology of contributing to the health of people by using germanium is necessary.

DISCLOSURE

Technical Problem

The present invention has been made in an effort to solve the problems of the conceptual description of the conventional art as described above, and an object of the present invention is to provide a device for generating and supplying germanium ionic water in that pulses are supplied to pure germanium rods of germanium for supplying ionized germanium ionic water, thereby significantly improving the concentration of germanium in a short time and shortening the solving time.

Another object of the present invention is to provide a device for generating and supplying germanium ionic water in that pure germanium ionic water can be quantitatively provided while maintaining a stable concentration and a stable content, by adjusting the concentration of the pure germanium ionic water.

Further another object of the present invention is to provide a device for generating and supplying germanium ionic water in that a sterilizing lamp, a cooling unit, and an agitator are formed at a water vessel, so that the pure germanium ionic water is sterilized, the heat generated in the water vessel is cooled, and the ionic water is uniformly mixed with the water.

Technical Solution

According to one aspect of the present invention so as to accomplish these objects, there is provided to a device for generating and supplying ionic water including:

a raw water supply pipe 110 that supplies raw water to a water vessel;

an ionic water discharge pipe 120 for discharging germanium ionic water to the outside;

a water level detection sensor 130 installed at a location of the interior of the water vessel to check an introduction state of the raw water and deliver a raw water detection signal to a main controller;

a water vessel 100 having an inlet for introducing the raw water supplied through the raw water supply pipe on one side thereof, having a first pure germanium rod 105 and a second pure germanium rod 105a connected through a connector, and having an outlet for supplying pure germanium ionic water produced through a reaction of the first pure germanium rod and the second pure germanium rod to the ionic water discharge pipe at one side thereof;

a concentration adjusting unit 200 for adjusting the concentration of the pure germanium ionic water under the control of a main controller; and a main controller 300 for providing an operation command for the concentration adjusting unit when the water level detection sensor acquires a raw water detection signal.

Advantageous Effects

According to the device for generating and supplying the germanium ionic water, there is an effect in that the pulses for repeatedly supplying and interrupting electric power per second are supplied to pure the germanium rods of germanium for supplying ionized germanium ionic water, thereby significantly improving the concentration of germanium in a short time and shortening the solving time.

Also, if necessary, there is another effect in that the pure germanium ionic water can be quantitatively provided while maintaining the stable concentration and the stable content, by adjusting the concentration of the pure germanium ionic water.

Moreover, there is further another effect in that the sterilizing lamp, the cooling unit, and the agitator are formed at the water vessel, so that the pure germanium ionic water is sterilized, the heat generated in the water vessel is cooled, and the ionic water is uniformly mixed with the water.

BRIEF DESCRIPTION OF DRAWINGS

The above and other objects, features and advantages of the present invention will be more apparent from the following detailed description taken in conjunction with the accompanying drawings, in which.

REFERENCE SIGNS LIST

Figure 1:
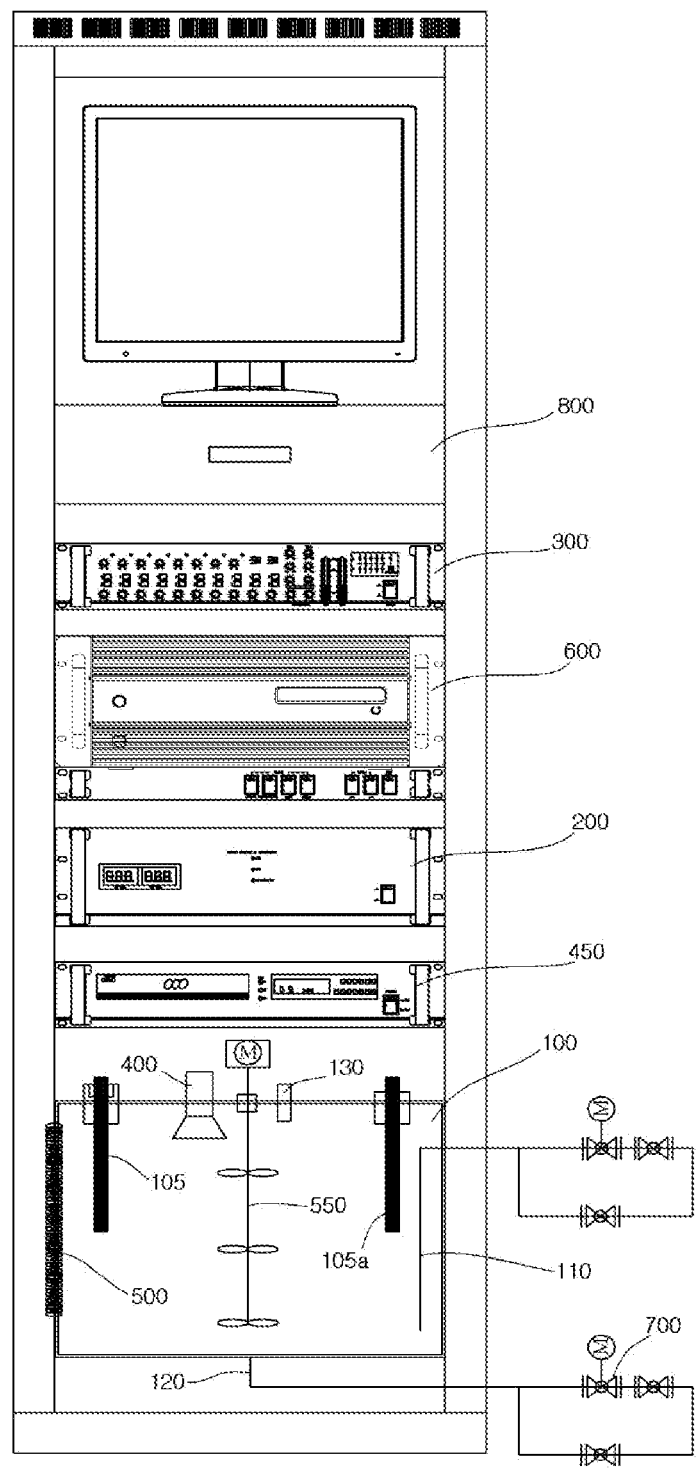
FIG. 1 is a schematic diagram illustrating a device for generating and supplying germanium ionic water according to an embodiment of the present invention.

100: water vessel
110: raw water supply pipe
120: ionic water discharge pipe
130: water level detection sensor
200: concentration adjusting unit
300: main controller
400: sterilizing lamp
450: sterilizing lamp power supply
500: cooling unit
550: agitator

BEST MODE

Mode for Invention

Hereinafter, a preferred embodiment according to the present invention will be described in detail with reference to the accompanying drawings.

FIG. 1 is a schematic diagram illustrating a device for generating and supplying germanium ionic water according to an embodiment of the present invention.

As illustrated in FIG. 1, the device for generating and supplying germanium ionic water according to the present invention includes:

a raw water supply pipe 110 that supplies raw water to a water vessel;

an ionic water discharge pipe 120 for discharging germanium ionic water to the outside;

a water level detection sensor 130 installed at a location of the interior of the water vessel to check an introduction state of the raw water and to deliver a raw water detection signal to a main controller;

a water vessel 100 having an inlet for introducing the raw water supplied through the raw water supply pipe on one side thereof, having a first pure germanium rod 105 and a second pure germanium rod 105a connected through a connector, and having an outlet for supplying pure germanium ionic water produced through a reaction of the first pure germanium rod and the second pure germanium rod to the ionic water discharge pipe at another side thereof;

a concentration adjusting unit 200 for adjusting the concentration of the pure germanium ionic water under the control of a main controller; and a main controller 300 for providing an operation command for the concentration adjusting unit when the water level detection sensor acquires a raw water detection signal.

Raw water including natural water, tap water, or underground water is supplied to the water vessel through the raw water supply pipe, and the supplied raw water is stored in the interior of the water vessel through the inlet of the water vessel.

The raw water is automatically or manually supplied to the water vessel through the raw water supply pipe by using an electric valve, a solenoid valve, or other manual valves, and when the system is automatic, the raw water is supplied or interrupted under the control of the main controller.

The ionic water discharge pipe 120 is installed on any side of the water vessel to discharge the completely reacted germanium ionic water to the outside.

Then, preferably, the solenoid valve 700 is installed in the ionic water discharge pipe to receive an opening signal transmitted by the main controller and discharge the pure germanium ionic water in the water vessel to the outside.

The water level detection sensor 130 is installed in the interior of the water vessel to check an introduction state of raw water and deliver a raw water detection signal to the main controller.

That is, if it is determined that the raw water reaches a predetermined height of the water vessel after the height of the raw water is detected, a raw water detection signal is transmitted to the main controller and the main controller provides an operation command for the concentration adjusting unit.

Further, a change value in the height of ionic water when the ionic water is discharged may be provided for the main controller.

An inlet for introducing the raw water supplied through the raw water supply pipe is formed on one side of the water vessel 100, and an outlet for providing the pure germanium ionic water produced by a reaction of the first pure germanium rod and the second pure germanium rod, to the ionic water discharge pipe is formed on another side of the water vessel 100.

Then, the first pure germanium rod and the second pure germanium rod, including the connector are installed in the interior of the water vessel for an ion reaction.

Pure germanium plates may be installed in addition to the pure germanium rod, and a modification of the shapes thereof also fall within the scope of the present invention.

If the water vessel is manufactured of a metal material, a germanium electrode and water react with each other so that electrons influence the metal components of the water vessel, corroding the interior of the water vessel and the metal components are mixed with ion components of pure germanium during a reaction of germanium ionic water and thus there is a difficulty in safely supplying the germanium ionic water, and accordingly, when the interior of the water vessel is inevitably manufactured of a metal material, a coating material through which an electric current does not flow and which is not harmful to the human body is coated on the interior of the water vessel or a transparent water vessel of a PE or ABS based material that is not harmful to the human body is used.

The water vessel is formed of a transparent material so that a reaction situation in the interior of the water vessel may be viewed.

A connector is used to prevent leakage of water from the pure germanium rods.

If an electric voltage is applied to a rod of germanium in the interior of the water vessel, an electrolytic reaction occurs, producing germanium.

Meanwhile, although it is exemplified in the drawing that various units are coupled to a system rack, the water vessel may be connected to a faucet if necessary, and it will be easily understood by those skilled in the art that the water vessel may be installed in other facilities that require ionic water.

The concentration adjusting unit 200 for adjusting the concentration of pure germanium ionic water is connected to the main controller.

Meanwhile, the main controller 300 may include a pulse number control unit 360 that controls the number of pulses for repeatedly supplying and interrupting electric power supplied by a raw water detection signal of the water level detection sensor per second.

That is, the number of pulses for repeatedly supplying and interrupting electric power per second is controlled.

The number of pulses is controlled because the concentration of raw water can be increased in a short time by electrolyzing raw water.

That is, an effect of splitting particles can be achieved if the raw water is supplied at several thousand pulses or several tens of thousands of pulses per second as described above, so that a problem in which raw water is easily solved and should stay in the water vessel for a long time and therefore the water vessel should have a large capacity can be solved.

Furthermore, although residues are stuck to the connector of the rod due to the raw water residing in a water vessel for a long time so that the residues cannot be easily solved and the water vessel should be frequently cleaned, the raw water does not stay in the water vessel for a long time according to the present invention and thus the difficulty in solving the residues and a troublesomeness of cleaning the water vessel can be eliminated.

The concentration adjusting unit adjusts voltage and current to adjust the concentration of pure germanium ionic water.

For example, the concentration adjusting unit is connected to the main controller to thicken the pure germanium ionic water by increasing an input voltage.

Through this, both a low voltage and a high voltage may be freely provided.

Although thermal water and mineral water melted in the natural system are produced over a long period of time, solving time can be shortened according to the present invention, and the pure germanium ionic water according to the present invention is ionized to produce ions, of which the sizes are smaller than the size of organic germanium and the ions melted in the germanium mineral water and the thermal water present in the natural system, and may be quantitatively provided at a stable concentration and a stable content because the effect and content of the pure germanium ionic water according to the present invention is remarkably high.

Furthermore, like natural germanium, the germanium according to the present invention undergoes a pharmacological action in the human body for 24 to 48 hours and then the total amount of the germanium is coupled to waste products, impurities, and heavy metals in the body and is discharged to the outside of the body through sweat and urine, which is safe.

Although germanium in the form of ions contained in mineral water and thermal water is safely taken, the prices of the mineral water and the thermal water are expensive so that ordinary persons cannot easily obtain them practically.

However, if the pure germanium ionic water is provided by using the device according to the present invention, everybody can easily obtain pure germanium ionic water at a low price, which contributes to the health of people and the citizens of the world.

The pure germanium described in the present invention means a high purity of 99.999% or more of germanium.

The total content of impurities per 1 kg of germanium is 1 ppm or less, which means a purity higher than that of the international standard, and the quality ensures a function beneficial to the human body even through the pure germanium according to the present invention is applied to any product.

The effects of germanium are as follows.

First, nutrients and oxygen are absolutely necessary in order that body cells may continue to repeatedly perform metabolisms while supplying oxygen to the human body (an oxygen replacement action), and when oxygen is lack, diseases such as chronic mono dioxide toxic symptoms, anemia, blood vessel disorders, heart disorders, low blood pressure, aging of cells, and metal disorders occur.

In recent years, it has been found in the experiments of medical scientists that germanium functions as an oxygen catalyst that helps efficient utilization of oxygen.

That is, it has been found by the modern medical science that if organic germanium is supplied to the human body, marginal oxygen gives vital forces to blood, and accordingly people may deviate from a chronic oxygen lack phenomenon.

Second, germanium provides a semiconductor action (adjustment of an electric current of body cells) or a negative ion effect, and generally, a material through which an electric current may flow well is called a good conductor, an object, such as glass or wood, which interrupts flow of an electric current is called an insulator, and a material that interrupts an electric current at a low temperature and passes an electric current well at a high temperature is called a semiconductor.

The most characteristic feature of germanium is an electrical property of a semiconductor having an intermediate property between a metal and a non-metal, and the property may cure many diseases of the human body so germanium is often called a miracle element.

That is, germanium has four electrons in the atomic structure, and germanium ions are easily coupled and are active in an electric current at the temperature of a human body.

If foreign substances are produced in the human body, the outermost electron of the four electrons falls into a negative (-) state and is discharged to the outside and the remaining three electrons fall into positive states to be harmonious with the human body.

The role of germanium is the very principle of curing the diseases of the human body, and is a principle of smoothening semiconductor flows of cells to cure diseases like acupuncture, moxa treatment, and acupressure performed in meridians or meridian points in the oriental medicals.

Third, the advantage of germanium is an immunity reinforcing operation of the human body, and the human body has two types of immune systems, in which the first is a system which feeds on pathogenic bacteria in the human body due to white blood cells and the second is a system that kills pathogenic bacteria while being coupled to the pathogenic bacteria having B-lymphocytes by T-lymphocytes due to an action by antibodies. Accordingly, a cancer means that the number of T-lymphocytes decreases, and it has been proved that germanium increases T-lymphocytes and restrains diseases by cancer cells, toxic materials, and viruses.

Fourth, the advantage of germanium is an interferon production inducing operation, and interferon is a protein containing sugar and is one of biological response modifiers (BRMs) produced by cells which is an anticancer and antivirus material discovered by Isaacs and Lindemann of the United Kingdom in 1957.

Interferon is a material that shows the most remarkable effect among the materials developed so far, which attacks cancer cells and restrains increase of cancer cells.

For example, interferon is administered as a B type hepatitis medicine.

Sato of Japanese has reported in a clinic experimental paper that germanium causes gamma interferon in the human body, and an experiment of professor Akiba has proved that the amount of taken germanium is proportional to the amount of produced interferon and has revealed that germanium induces production of interferon in the human body.

Fifth, the advantage of germanium is an endorphin production expediting operation, and because organic germanium functions as an oxygen catalyst that helps an efficient utilization of oxygen of the human body, the amount of oxygen for cells is decreased if germanium is supplied to the human body so that oxygen is left in the human body after being used and expedite production of endorphin that is a natural medicine of the human body.

Accordingly, germanium rapidly recovers fatigues, solves a chronic oxygen deficiency, and provides a clear spirit.

Sixth, the advantage of germanium is a pain removing operation, and if a pain sensing phenomenon occurs at any portion of the human body, a ferment called enkiprarines is produced in the brain and a pain restraining material called enkeprarin is melt away so that the brain can recognize pains.

Accordingly, most of analgesics temporarily restrain the enkeprarines ferment, and if the effect of the analgesic disappears, pains are felt again, showing side effects and addiction symptoms, but germanium slowly shows an effect and does not have a side effect although not showing an instantaneous effect like the analgesics.

Seventh, the advantage of germanium is a toxic removing operation and a heavy metal discharging operation, and because organic germanium suctions toxic materials and is chemically coupled to the toxic materials to perform a toxic removing operation of producing another material without toxics due to a chemical feature of having oxygen atoms of a strong oxidation property.

In particular, germanium is excellent in removal of contaminants of heavy metals such as mercury and cadmium, and because all smokers are addicted to cadmium, germanium removes toxics from the smokers very efficiently.

Eighth, the advantage of germanium is a natural curing force improving operation, and all living things including humans are equipped with natural curing forces by nature, and have an instinctive operation of returning to the original state when they are injured or have troubles.

Because germanium improves a natural curing force in the human body, it has an effect of curing modern incurable diseases that cannot be cured by medicines.

Ninth, the advantage of germanium is a dehydrogenation operation, and hydrogen generated when foods are digested is a positive ion and totally useless in the human body, and if a large amount of hydrogen is present in the human body, the human body is acid, which is scaled by pH and the acidic property is strong if the pH is low.

Accordingly, the hydrogen ions cause all diseases by making the human body acid, and because organic germanium is converted into water instead of oxygen and is discharged, the physical constitution becomes alkali to prevent diseases.

The object of the present invention is to provide germanium having the aforementioned effect for ionic water.

Meanwhile, according to another aspect of the present invention, the device of the present invention may further include a sterilizing lamp 400 installed on the upper side of the vessel to sterilize pure germanium ionic water; and a sterilizing lamp power supply 450 for supplying electric power to the sterilizing lamp under the control of the main controller.

The sterilizing lamp 400 is installed on the upper side of the water vessel to sterilize pure germanium ionic water.

To achieve this, the sterilizing lamp power supply 450 is provided to supply electric power to the sterilizing lamp under the control of the main controller.

That is, the sterilizing lamp is used for sanitation of the ionic water in the water vessel and sterilization of germs in germanium ionic water.

Meanwhile, the device according to another aspect of the present invention may further include:

a cooling unit 500 installed in the interior of the water vessel to cool heat generated in the water vessel under the control of the main controller during a reaction of pure germanium ionic water; and an agitator 550 installed on the outside of the cooling unit at a predetermined interval to have a propeller shape to uniformly agitate ionic water and water under the control of the main controller during a reaction of the pure germanium ionic water to maintain the concentration of the ionic water constantly.

That is, the cooling unit 500 is provided to cool the heat generated by the water vessel.

Heat is generated in the interior of the water vessel in an electrolytic process of the germanium ionic water, and then heat in the interior of the water vessel is cooled by using a coolant or other cooling systems.

The cooling unit may be independently installed in the water vessel, and in another example, a rod is installed in the water vessel and an agitator may be installed in the rod.

The agitator 550 is installed on the outside of the cooling unit at a predetermined interval to have a propeller shape, and ionic water and water are uniformly agitated under the control of the main controller during a reaction of the pure germanium ionic water to maintain the concentration of the ionic water constantly.

The agitator has a propeller shape and is formed of a material other than a metal that is not harmful to the human body, and agitates ionic water and water during an ionic reaction to mix the ionic water and the water and maintain the concentration of the ionic water constantly.

An ion concentration analyzer 600 analyzes the concentration of pure germanium ionic water to provide the concentration value for the main controller.

That is, the ion concentration analyzer 600 provides the concentration value of the ionic water for the main controller and identifies whether the concentration value of the ionic water is the same as a set concentration value if necessary.

Figure 2:
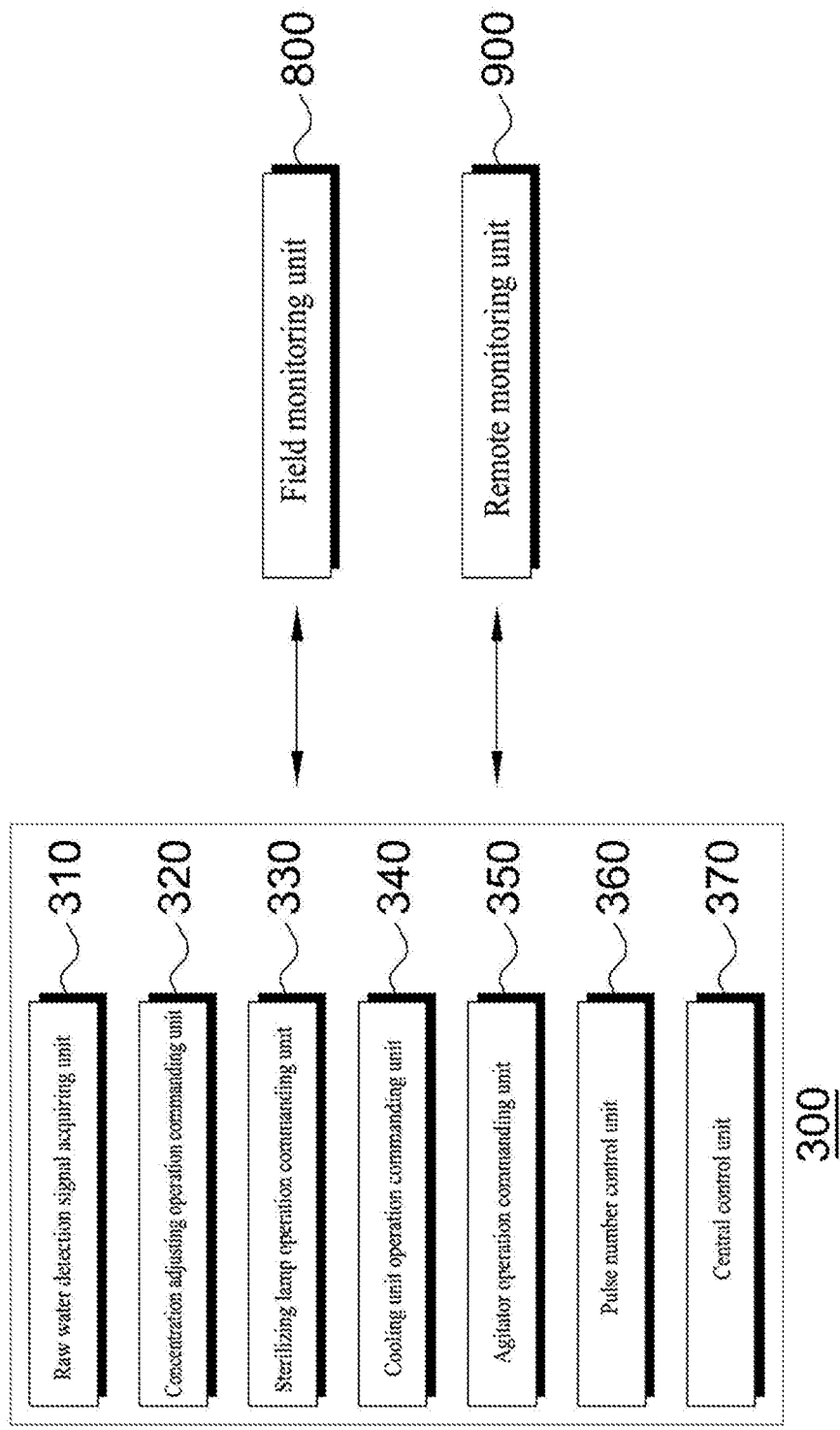
FIG. 2 is a block diagram of a main controller of the device for generating and supplying germanium ionic water according to the embodiment of the present invention.

FIG. 2 is a block diagram of a main controller of the device for generating and supplying germanium ionic water according to the embodiment of the present invention.

As illustrated in FIG. 2, the main controller 300 includes:

a raw water detection signal acquiring unit 310 for acquiring a raw water detection signal of the water level detection sensor;

a concentration adjusting operation commanding unit 320 for acquiring a concentration manipulation signal and providing an operation command for the concentration adjusting unit;

a sterilizing lamp operation commanding unit 330 for controlling supply of electric power to the sterilizing lamp power supply;

a cooling unit operation commanding unit 340 for providing an operation command for the cooling unit during a reaction of the pure germanium ionic water; and an agitator operation commanding unit 350 for providing an operation command for the agitator during a reaction of the pure germanium ionic water.

Then, generally, it is natural that a central control unit 370 be provided to perform an overall control of the device.

The raw water detection signal acquiring unit 310 acquires a raw water detection signal of the water level detection sensor.

For example, if the level of water is set to 10, it is detected whether the raw water is supplied up to the corresponding level.

If the level of the raw water reaches the corresponding level, the central control unit transmits a control signal to the concentration adjusting operation commanding unit 320 and the concentration adjusting operation commanding unit 320 acquires a concentration manipulation signal and provides an operation command for the concentration adjusting unit.

The concentration manipulation signal means a concentration value set in advance by the operator.

Then, the ion concentration analyzer analyzes the concentration of pure germanium ionic water to provide the concentration value for the main controller.

That is, the ion concentration analyzer analyzes whether the concentration of the pure germanium ionic water reaches a set concentration value.

The sterilizing lamp operation commanding unit 330 controls supply of electric power to the sterilizing lamp power supply during an operation of the concentration adjusting unit.

That is, the central control unit transmits a control signal, the sterilizing lamp operation commanding unit provides a power supply signal for the sterilizing lamp power supply, and the sterilizing lamp power supply is operated to allow the sterilizing lamp to perform a sterilizing operation.

The cooling unit operation commanding unit 340 provides an operation command for the cooling unit according to a control signal provided by the central control unit during a reaction of the pure germanium ionic water, that is, during an operation of the concentration adjusting unit.

Then, if receiving a control signal of the central control unit, the agitator operation commanding unit 350 provides an operation command for the agitator to allow the agitator to perform an agitating operation.

Meanwhile, it is possible to install only the concentration adjusting unit, the main controller, and the water vessel such that the device may be used at home or at a bathhouse.

Meanwhile, according to another aspect of the present invention, the device may further include a field monitoring unit 800 for acquiring an operation command state of the main controller to provide the acquired operation command state for the screen, and providing a control signal for the main controller; and a remote monitoring unit 900 installed remotely to acquire an operation command state of the main controller to provide the acquired operation command state, and to provide a control signal for the main controller for the screen.

That is, the field monitoring unit is provided as in the drawing to acquire an operation command state of the main controller to provide the acquired operation command state for a screen, and to provide a control signal for the main controller.

Furthermore, if a setting screen that may be set by the operator is provided such that the concentration value of the germanium ionic water is set, a state value for the corresponding command is acquired and is provided for a screen if the main controller automatically performs an operation command.

For example, it is identified whether, currently, the concentration adjusting unit is operated, electric power is supplied, and the sterilizing lamp and the cooling unit are operated.

Further, the device may be collectively managed in a remote site as well as in the field when the device is a large-scale one or a plurality of devices are provided.

To achieve this, the remote monitoring unit 900 may be connected to the main controller such that the state of the main controller may be identified in a remote site, and a control signal maybe transmitted for the main controller at a remote site if necessary to remotely control the device.

In order to supply the germanium ionic water ionized through the above-described configurations and operations, pulses for repeatedly supplying and interrupting electric power per second is supplied to the pure germanium rods formed of germanium, significantly improving the concentration of germanium in a short time and shortening solving time.

In addition, according to occasions, pure germanium ionic water can be quantitatively provided while maintaining a stable concentration and a stable content, by adjusting the concentration of the pure germanium ionic water.

While the present invention has been described with respect to the specific embodiments, it will be apparent to those skilled in the art that various changes and modifications may be made without departing from the spirit and scope of the present invention as defined in the following claims.

What is claimed is:

1. A device for generating and supplying ionic water comprising:

a raw water supply pipe (110) that supplies raw water to a water vessel;

an ionic water discharge pipe (120) for discharging germanium ionic water to the outside;

a water level detection sensor (130) installed at a location of the interior of the water vessel to check an introduction state of the raw water and deliver a raw water detection signal to a main controller;

a water vessel (100) having an inlet for introducing the raw water supplied through the raw water supply pipe on one side thereof, having a first pure germanium rod (105) and a second pure germanium rod (105a) connected through a connector, and having an outlet for supplying pure germanium ionic water produced through a reaction of the first pure germanium rod and the second pure germanium rod to the ionic water discharge pipe at one side thereof;

a concentration adjusting unit (200) for adjusting the concentration of the pure germanium ionic water under the control of a main controller;

a main controller (300) for providing an operation command for the concentration adjusting unit when the water level detection sensor acquires a raw water detection signal; and a cooling unit (500) installed in the interior of the water vessel to cool heat generated in the water vessel under the control of the main controller during a reaction of pure germanium ionic water.

2. A device for generating and supplying ionic water comprising:
- a raw water supply pipe (110) that supplies raw water to a water vessel;
- an ionic water discharge pipe (120) for discharging germanium ionic water to the outside;
- a water level detection sensor (130) installed at a location of the interior of the water vessel to check an introduction state of the raw water and deliver a raw water detection signal to a main controller;
- a water vessel (100) having an inlet for introducing the raw water supplied through the raw water supply pipe on one side thereof, having a first pure germanium rod (105) and a second pure germanium rod (105*a*) connected through a connector, and having an outlet for supplying pure germanium ionic water produced through a reaction of the first pure germanium rod and the second pure germanium rod to the ionic water discharge pipe at one side thereof;
- a concentration adjusting unit (200) for adjusting the concentration of the pure germanium ionic water under the control of a main controller;
- a main controller (300) for providing an operation command for the concentration adjusting unit when the water level detection sensor acquires a raw water detection signal;
- a cooling unit (500) installed in the interior of the water vessel to cool heat generated in the water vessel under the control of the main controller during a reaction of pure germanium ionic water; and
- an agitator (550) installed on the outside of the cooling unit at a predetermined interval to have a propeller shape to uniformly agitate ionic water and water under the control of the main controller during a reaction of the pure germanium ionic water to maintain the concentration of the ionic water constantly.

3. The device for generating and supplying ionic water as claimed in claim 1, wherein the main controller (300) comprises:
- a raw water detection signal acquiring unit (310) for acquiring a raw water detection signal of the water level detection sensor;
- a concentration adjusting operation commanding unit (320) for acquiring a concentration manipulation signal and providing an operation command for the concentration adjusting unit;
- a sterilizing lamp operation commanding unit (330) for controlling supply of electric power to the sterilizing lamp power supply;
- a cooling unit operation commanding unit (340) for providing an operation command for the cooling unit during a reaction of the pure germanium ionic water; and
- an agitator operation commanding unit (350) for providing an operation command for the agitator during a reaction of the pure germanium ionic water.

\* \* \* \* \*